United States Patent [19]

Naruse et al.

[11] Patent Number: 5,210,817
[45] Date of Patent: May 11, 1993

[54] ACTUATOR

[75] Inventors: Yoshihiro Naruse, Ichikawa; Tomokimi Mizuno, Chiryu; Mitsuhiro Ando; Naomasa Nakajima, both of Tokyo, all of Japan

[73] Assignee: Aisin Seiki Kabushiki Kaisha, Kariya, Japan

[21] Appl. No.: 851,526

[22] Filed: Mar. 16, 1992

[30] Foreign Application Priority Data

Mar. 19, 1991 [JP] Japan .................................. 3-78343

[51] Int. Cl.$^5$ ............................................ G02B 6/26
[52] U.S. Cl. .................................................. 385/147
[58] Field of Search .................... 385/16, 147, 76, 77

[56] References Cited

U.S. PATENT DOCUMENTS

4,974,922 12/1990 Mori ..................................... 385/147
4,984,860 1/1991 Seike et al. ......................... 385/147
5,061,026 10/1991 Clarke et al. ........................ 385/31
5,101,470 3/1992 Reynolds ............................. 385/147

Primary Examiner—Frank Gonzalez
Attorney, Agent, or Firm—Finnegan, Henderson, Farabow, Garrett & Dunner

[57] ABSTRACT

An actuator is comprised of a main body having an opening at its one side, an inner space defined within the main body and filled with an amount of thermally expansive gas, a substance for converting the light into the heat which is accommodated in the inner space, a guide device for guiding light into the second portion of the inner space, and a membrane connected to the side of the main body for closing the opening and deflected previously toward the inner space so as to establish a snap action toward outward of the main body when the inner pressure exceed a set value.

3 Claims, 5 Drawing Sheets

ACTUATOR

BACKGROUND OF THE INVENTION

The present invention relates to an actuator and in particular to an actuator for operating a relatively minute device such as a chatheter, a manipulator for operating the cell or a manipulator for operating a robot to be used in a narrow space.

An actuator of the kind or a related actuator, which is disclosed in U.S. patent application Ser. No. 07/764,677 (still pending) as a related application of the instant application, includes a main body having an inner space with an opening, a thin film member connected to the main body for closing the inner space, an amount of thermally expansive gas filled in the inner space, a substance for converting the light into the heat which is accommodated in the inner space, and a controller having a device for guiding the light into the inner space.

In the foregoing actuator, upon application of the light into the inner space of the main body, heat at a degree is generated, and the resultant heat brings the gas into expansion. Thus, the thin film is deformed and the resultant deformation is set to be used as a force for driving a specific element.

However, the foregoing deformation which is read as a displacement of the thin film member is too small to be practical use, which results in that the actuator can be used only in the limited fields.

SUMMARY OF THE INVENTION

It is, therefore, a primary object of the present invention to provide an improved actuator without the foregoing drawback.

It is another object of the present invention to provide an actuator in which a thin film member can be deformed sufficiently so as to be practical use.

In order to attain the foregoing objects, an actuator is comprised of a main body having an opening at its one side, an inner space defined within the main body and filled with an amount of thermally expansive gas, a substance for converting the light into the heat which is accommodated in the inner space, guide means for guiding light into the second portion of the inner space, and a membrane connected to the side of the main body for closing the opening and deflected previously toward the inner space so as to establish a snap action toward outward of the main body when the inner pressure exceed a set value.

BRIEF DESCRIPTION OF THE DRAWINGS

The above and other objects, features and advantages of the present invention will be more apparent and more readily appreciated from the following detailed description of preferred exemplarily embodiment of the present invention, taken in connection with the accompanying drawings, in which.

DESCRIPTION OF THE PREFERRED EMBODIMENT

Referring to FIGS. 1, 2, 3(a), 3(b), and 5, there is illustrated an actuator or a silicon diaphragm 1 which is to be used as an extremely minituarized pincette. The actuator 1 includes a main body 7 which is comprised of a pair of mutually connected members 7a and 7b made of silicon. An inner space 20 is defined within the main body 7 in which an amount of thermally expandable gas 10 is filled and a carbon fiber 8 as a substance for converting the light into the heat is accommodated. As the gas 10, one with a low boiling point is available such as flon-11, flon-113, ethanol, methanol or diethylethanl.

Figure 1:
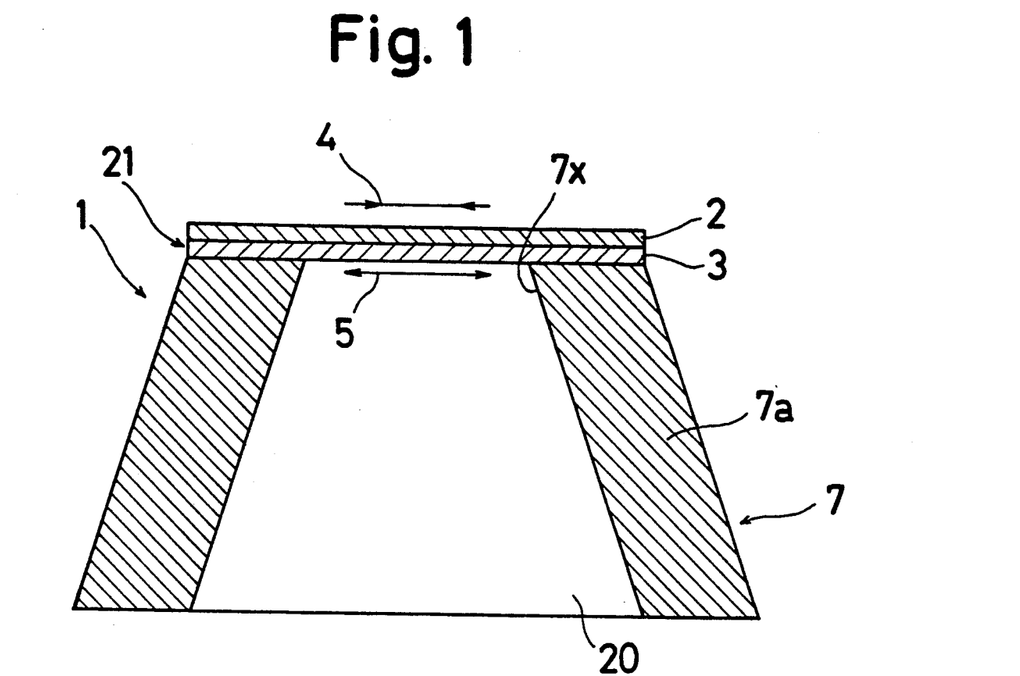
FIG. 1 is an enlarged cross-sectional view of an upper half portion of a main body of an actuator according to an embodiment of the present invention.
Figure 2:
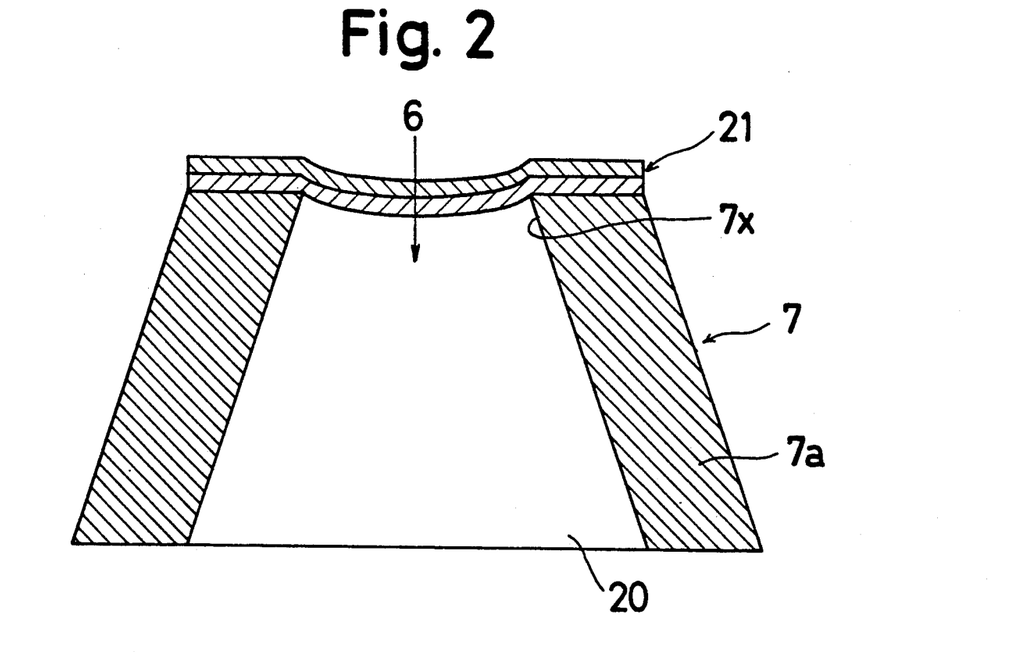
FIG. 2 is a view which shows the mechanism of a deflection of a membrane.
Figure 3A:
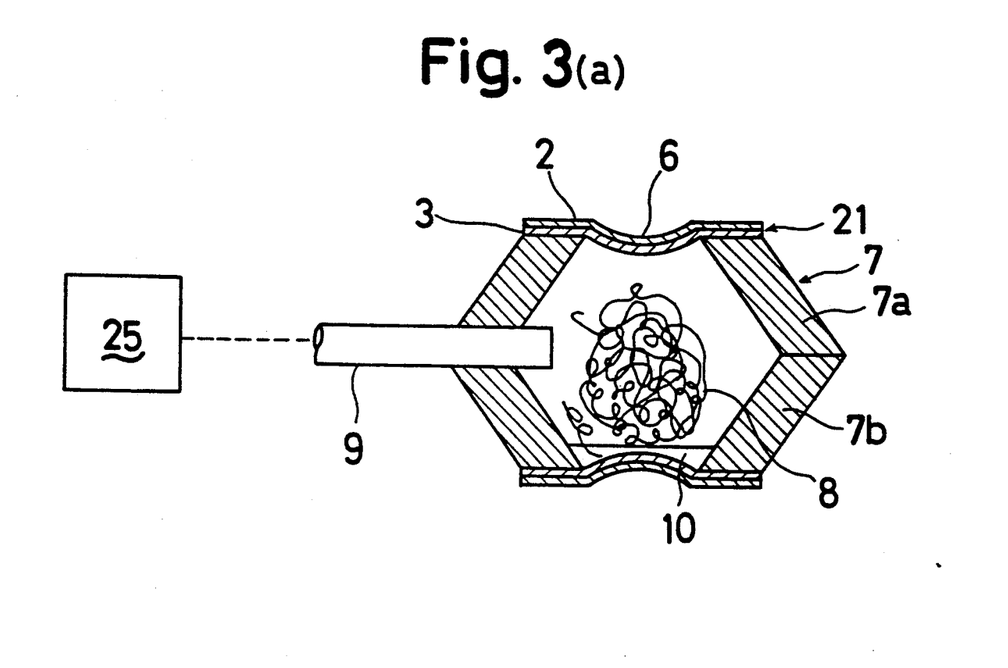
FIG. 3(a) shows an initial condition of each membrane.
Figure 3B:
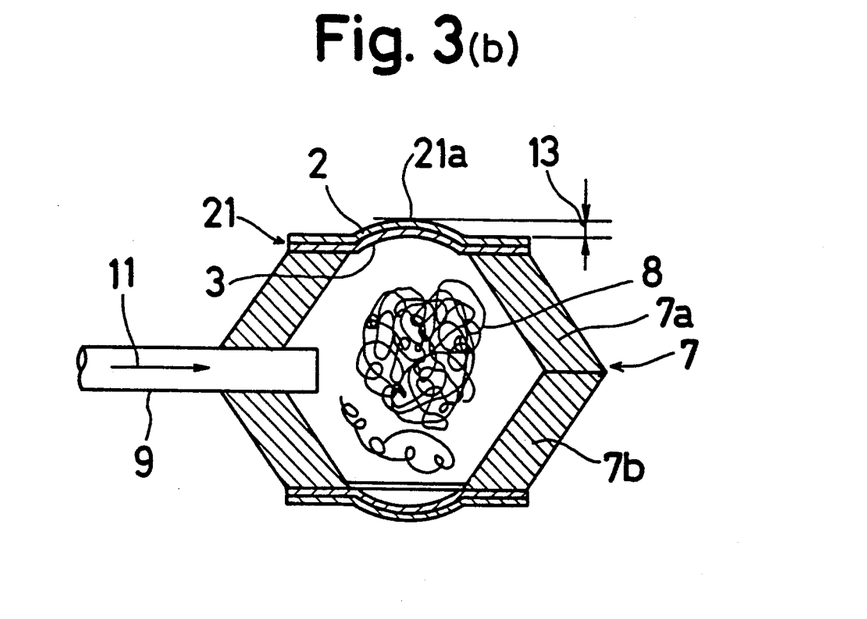
FIG. 3(b) shows a expanded condition of each membrane.

An upper opening 7x of the upper portion 7a of the main body 7 is closed by a membrane 21 which is in layer of a first thin film 2 and a second thin film 3. The first thin film 2 is set to be larger than the second thin film 3 in the thermal expansion coefficient so as to develop or generate a residual tension stress 4 in the first thin film 2 and a residual compress stress 5 in the second thin film 3. This causes a deflection of the membrane 21 toward the inner space 20. A similar structure is established at the lower member 7b of the main body 7. An optical fiber 9 as a light guide menas is extended into the inner space 20 so as to receive the light such as laser light 11 from a controller 25 as a light source.

When the laser light 11 is transmitted into the inner space 20 from the controller 25 through the optical fiber 9, the carbon fiber 8 is heated up to a temperature and the resultant heat also warms the gas 10. Then, an inner pressure in the inner space 20 is increased and the resulting pressure is applied to each membrane 21. Thus, each membrane 21 is deformed in the outward direction from an initial condition shown in FIG. 3(a) to an expanded condition FIG. 3(b). In light of the fact that each membrane 21 is, in its initial condition, bent or deflected previously in the downward direction, under the expanded condition, a displacement 13 of the membrane 21 which is defined as the height difference between a top portion 21a and a flat portion 21b of the membrane 21 becomes larger than a displacement of the conventional membrane which is flat in its initial condition.

The following steps are those of the manufacturing process of the foregoing the upper member 1.

Figure 4A:
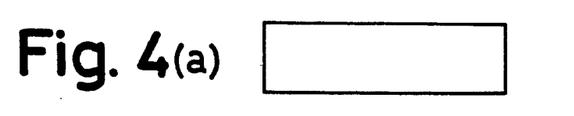
FIGS. 4a through 4f show a series of steps for producing an upper half portion of an actuator.

(1) First of all, a raw material of the upper member 7a of the main body 7 is prepared in the form of a substrate (FIG. 4a).

Figure 4B:
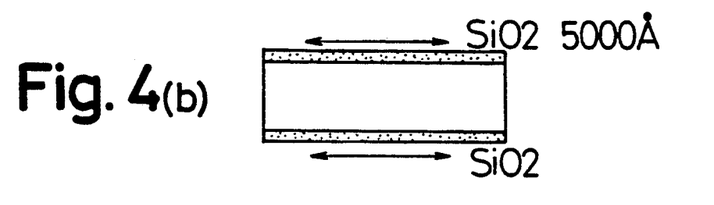

(2) A thin film of acid ($SiO_2$) with a thickness of 5000 Å is formed on each surface of the substrate (FIG. 4b). It is to be noted this thin film corresponds to the second thin film 3.

Figure 4C:
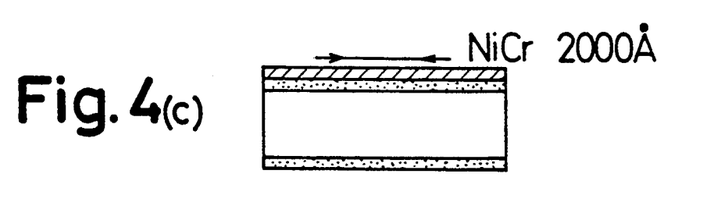

(3) A metal film of NiCr with a thickness of 2000 Å is formed on the upper thin film of acid ($SiO_2$) by sputtering (FIG. 4c). It is to be noted this thin film corresponds to the first thin film 2.

Figure 4D:
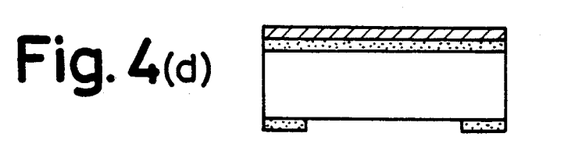

(4) Patternning is established in the lower thin film of acid ($SiO_2$) (FIG. 4d).

Figure 4E:
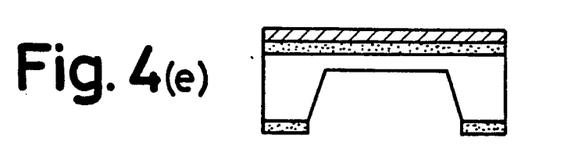

(5) Wet etching or aeolotropy etching by alkaline liquid is made on the lower thin film of acid ($SiO_2$) so as to define a half of the inner space (FIG. 4e).

Figure 4F:
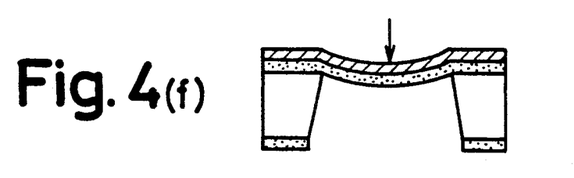
Figure 5:
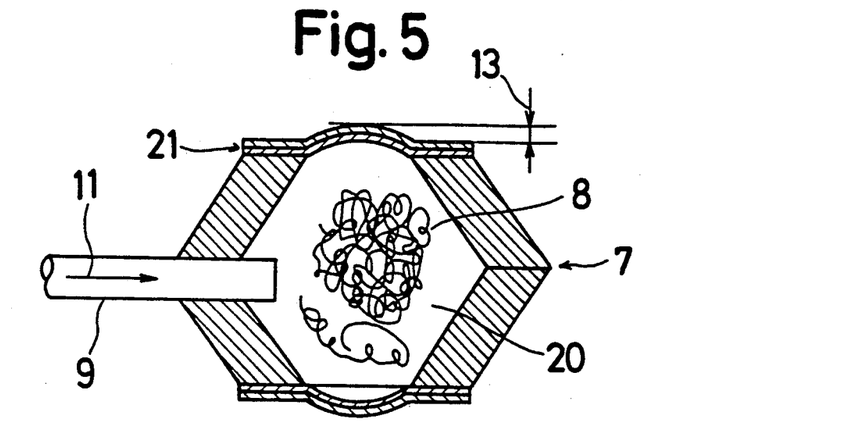
FIG. 5 is a cross-sectional view of an actuator which is in operation.

(6) The upper half 7a of the main body 7 with the deflected membrane 3 is obtained (FIG. 4f).

Figure 6:
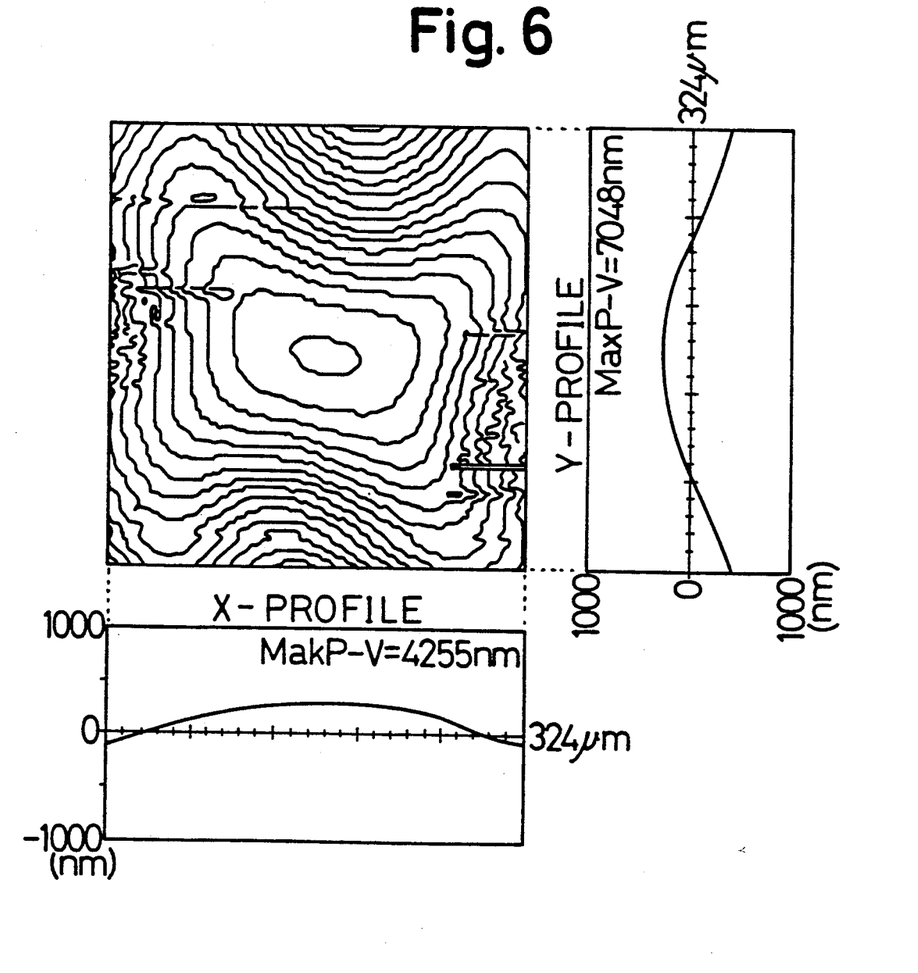
FIG. 6 is a contour line map of a configuration of a membrane.
Figure 7:
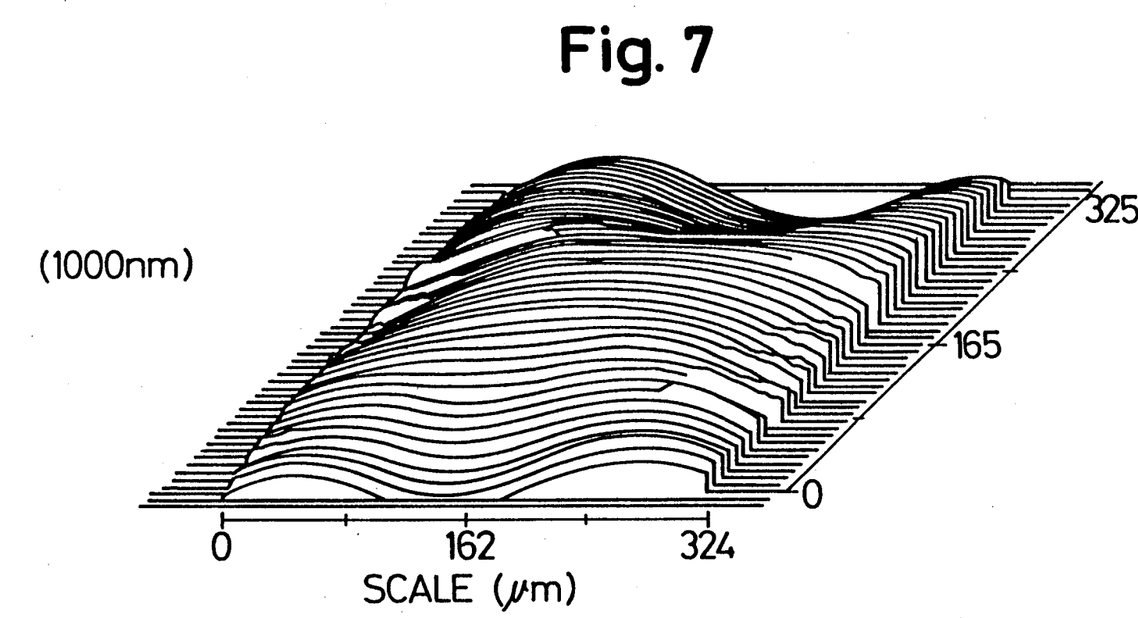
FIG. 7 is a three-dimension model of a membrane.

The resulting membrane 21 is illustrated in the form of a contour line map and a three-dimension model as shown in FIG. 6 and FIG. 7, respectively. According to these illustrations, if the membrane 21 is of a regular square shape with a side of 400 mm, the membrane 21 makes or constitutes a mountain in such a manner that its central portion corresponds to the top of the mountain and the maximum value of the displacement 13 ranges from 4 µm to 7 µm.

It is to be noted that residual stress between two thin films in the membrane has a tendency to return the deflected condition of the membrane to its initial state which enables the quick response action of the actuator.

In addition, the snap action of each membrane 21 can be obtained by other suitable means.

It should be apparent to one skilled in the art that the above-described embodiment is merely illustrative of but a few of the many possible specific embodiments of the present invention. Numerous and various other arrangements can be readily devised by those skilled in the art without departing from the spirit and scope of the invention as defined in the following claims.

What is claimed is:

1. An actuator comprising:
   a main body having an opening at its one side;
   an inner space defined within the main body and filled with an amount of thermally expansive gas;
   a substance for converting the light into the heat which is accommodated in the inner space;
   guide means for guiding light into the second portion of the inner space; and
   a membrane connected to the side of the main body for closing the opening and deflected previously toward the inner space so as to establish a snap action toward outward of the main body when the inner pressure exceed a set value.

2. An actuator according to claim 1, wherein the membrane is in the form of two layers of thin films of different thermal expansive coefficient.

3. An acutator according to claim 2, wherein raw materials of the films are $SiO_2$ and NiCr.

* * * * *

UNITED STATES PATENT AND TRADEMARK OFFICE
CERTIFICATE OF CORRECTION

PATENT NO. : 5,210,817

DATED : May 11, 1993

INVENTOR(S) : Yoshihiro Naruse, et al.

It is certified that error appears in the above-indentified patent and that said Letters Patent is hereby corrected as shown below:

The sheets of drawings consisting of figures 6-7, should be deleted to appear as per attached sheets.

Signed and Sealed this

Fifth Day of April, 1994

Attest:

BRUCE LEHMAN

*Attesting Officer*   *Commissioner of Patents and Trademarks*

UNITED STATES PATENT AND TRADEMARK OFFICE
CERTIFICATE OF CORRECTION

PATENT NO. : 5,210,817

DATED : May 11, 1993

INVENTOR(S) : Yoshihiro NARUSE et al.

It is certified that error appears in the above-identified patent and that said Letters Patent is hereby corrected as shown below:

Fig. 6

UNITED STATES PATENT AND TRADEMARK OFFICE
CERTIFICATE OF CORRECTION

PATENT NO. : 5,210,817

DATED : May 11, 1993

INVENTOR(S) : Yoshihiro NARUSE et al.

It is certified that error appears in the above-identified patent and that said Letters Patent is hereby corrected as shown below:

Fig. 7